(12) United States Patent
Kidane et al.

(10) Patent No.: US 7,611,728 B2
(45) Date of Patent: Nov. 3, 2009

(54) OSMOTIC DELIVERY OF THERAPEUTIC COMPOUNDS BY SOLUBILITY ENHANCEMENT

(75) Inventors: Argaw Kidane, Montgomery Village, MD (US); Shimul K. Ray, Alexandria, VA (US); Padmanabh P. Bhatt, Rockville, MD (US); Jones W. Bryan, Jr., Gaithersburg, MD (US)

(73) Assignee: Supernus Pharmaceuticals, Inc., Rockville, MD (US)

( * ) Notice: Subject to any disclaimer, the term of this patent is extended or adjusted under 35 U.S.C. 154(b) by 740 days.

(21) Appl. No.: 10/655,725

(22) Filed: Sep. 5, 2003

(65) Prior Publication Data
US 2005/0053653 A1    Mar. 10, 2005

(51) Int. Cl.
*A61K 9/20*    (2006.01)
(52) U.S. Cl. .................................................... 424/465
(58) Field of Classification Search ................ 424/465
See application file for complete search history.

(56) References Cited

U.S. PATENT DOCUMENTS

| | | | |
|---|---|---|---|
| 4,036,228 | A | 7/1977 | Theeuwes |
| 4,077,407 | A | 3/1978 | Theeuwes et al. |
| 4,160,020 | A | 7/1979 | Ayer et al. |
| 4,327,725 | A | 5/1982 | Cortese et al. |
| 4,609,374 | A | 9/1986 | Ayer |
| 4,612,008 | A | 9/1986 | Wong et al. |
| 4,615,698 | A | 10/1986 | Guittard et al. |
| 4,765,989 | A | 8/1988 | Wong et al. |
| 4,783,337 | A | 11/1988 | Wong et al. |
| 4,801,461 | A | 1/1989 | Hamel et al. |
| 4,992,278 | A | 2/1991 | Khanna |
| 5,422,123 | A | 6/1995 | Conte et al. |
| 5,484,608 | A | 1/1996 | Rudnic et al. |
| 5,545,413 | A | 8/1996 | Kuczynski et al. |
| 5,612,059 | A | 3/1997 | Cardinal |
| 5,697,922 | A * | 12/1997 | Thombre ................. 604/892.1 |
| 5,698,220 | A | 12/1997 | Cardinal et al. |
| 5,827,538 | A * | 10/1998 | Cussler et al. .............. 424/473 |
| 6,004,582 | A | 12/1999 | Faour et al. |
| 6,110,498 | A | 8/2000 | Rudnic et al. |
| 6,284,276 | B1 | 9/2001 | Rudnic et al. |
| 6,352,721 | B1 | 3/2002 | Faour |
| 6,361,796 | B1 | 3/2002 | Rudnic et al. |
| 6,491,949 | B2 | 12/2002 | Faour et al. |
| 6,514,532 | B2 | 2/2003 | Rudnic et al. |
| 6,521,255 | B2 | 2/2003 | Vergez |
| 6,569,456 | B2 | 5/2003 | Faour |
| 6,572,890 | B2 | 6/2003 | Faour |
| 6,599,284 | B2 | 7/2003 | Faour |
| 6,599,532 | B2 | 7/2003 | Faour |
| 6,605,302 | B2 | 8/2003 | Faour |
| 6,613,357 | B2 | 9/2003 | Faour |
| 6,753,011 | B2 | 6/2004 | Faour |
| 7,008,641 | B2 | 3/2006 | Faour |
| RE39,069 | E | 4/2006 | Faour |
| 7,147,870 | B2 | 12/2006 | Faour |
| 7,208,176 | B2 | 4/2007 | Faour |
| 2004/0091529 | A1 * | 5/2004 | Edgren et al. ................ 424/468 |

FOREIGN PATENT DOCUMENTS

| | | |
|---|---|---|
| WO | WO 95/03033 | 2/1995 |
| WO | WO 03/092660 | 11/2003 |
| WO | WO 2004/002447 | 1/2004 |
| WO | WO 2004/098572 | 11/2004 |

OTHER PUBLICATIONS

U.S. Appl. No. 60/392,128, filed Jun. 26, 2002, Edgren.

* cited by examiner

*Primary Examiner*—Gollamudi S. Kishore
*Assistant Examiner*—Snigdha Maewall
(74) *Attorney, Agent, or Firm*—Arent Fox LLP; Anna Ganelina (57) ABSTRACT

The present invention is directed to the oral osmotic delivery of therapeutic compounds that have limited solubility in an aqueous environment due to inherent hydrophobicity or to saturation limitations in the core of the osmotic system. The present invention is suitable for the osmotic delivery of glipizide and other hydrophobic drugs, but runs the spectrum to other therapeutic agents with higher aqueous solubilities, yet having a solubility limitation in an osmotic dosage unit due to high drug load.

17 Claims, 10 Drawing Sheets

OSMOTIC DELIVERY OF THERAPEUTIC COMPOUNDS BY SOLUBILITY ENHANCEMENT

FIELD OF THE INVENTION

The present invention is directed to the oral osmotic delivery of therapeutic compounds that have limited solubility in an aqueous environment due to inherent hydrophobicity or to saturation limitations in the core of the osmotic system. The present invention is suitable for the osmotic delivery of glipizide and other hydrophobic drugs, but runs the spectrum to other therapeutic agents with higher aqueous solubilities, yet having a solubility limitation in an osmotic dosage unit due to high drug load.

BACKGROUND OF THE INVENTION

Extended release tablets that have an osmotically active drug core surrounded by a semipermeable membrane are known in the art. These osmotic dosage forms function by allowing water, from gastric or intestinal fluid, to flow through the semipermeable membrane and dissolve the active ingredient in the core so it can be released through one or more passageways created in the membrane. An elementary osmotic delivery system requires that the drug be in solution in order to be delivered in a controlled and predictable manner. The drug in solution is pumped out due to the osmotic gradient generated across the semipermeable membrane.

If the drug is insoluble, an elementary osmotic system will not function properly. One approach for delivering pharmaceutical agents that are insoluble in aqueous solvents was developed by Kuczynski et al., (U.S. Pat. No. 5,545,413). In their approach, the interior of the tablet or capsule is characterized by two core layers, one containing the pharmaceutical agent (again to be released through openings, or holes, in the wall of the tablet or capsule) and the other being a layer of material that swells when coming into contact with water. The material that swells or expands to an equilibrium state when exposed to water or other biological fluids is referred to as an "osmopolymer". This volume expansion is used to physically force the pharmaceutical agent out through openings, which have been formed in the wall, shell or coating during manufacture. The pharmaceutical agent is primarily released as insoluble particles, which therefore have limited bioavailability. This has commonly been referred to as the "push/pull" approach. See, for example, U.S. Pat. Nos. 5,422,123; 4,783,337; 4,765,989; 4,612,008; and 4,327,725. The patent literature has taught that this approach was necessary to deliver adequate doses, at controlled rates and for extended times, of a broad variety of drugs.

Other osmotic delivery systems have also been described. See, for example, U.S. Pat. Nos. 4,609,374; 4,036,228; 4,992,278; 4,160,020; and 4,615,698. The osmopolymers used in these types of systems are components whose functions are to swell when they interact with water and aqueous fluids. This swelling effect is defined in these patents as a property of imbibing fluid so as to expand to a very high degree, usually exhibiting a 2 to 50-fold volume increase.

Rudnic et al., (U.S. Pat. Nos. 6,110,498; 6,284,276; 6,361,796, and 6,514,532) used sodium lauryl sulfate and other solubilizers to enhance the solubility of glipizide, a poorly soluble drug, to deliver it from an elementary type of osmotic system in a sustained manner. This system of Rudnic is comprised of (a) a semi-permeable wall that maintains its integrity during pharmaceutical delivery and which has at least one passage there through; (b) a single, homogeneous composition within said wall, which composition consists essentially of (i) a pharmaceutically active agent, (ii) at least one non-swelling solubilizing agent which enhances the solubility of the pharmaceutically active agent; (iii) at least one non-swelling osmotic agent, and, optionally, (iv) a non-swelling wicking agent dispersed throughout the composition which enhances the surface area contact of the pharmaceutical agent with the incoming aqueous fluid.

A limitation of the system of Rudnic is that none of the solubilizers disclosed are capable of fully solubilizing glipizide, an example of a hydrophobic active agent, in the core after the osmotic pill is ingested. Although this system provided improvements to the state of the art, this limitation may lead to erratic and unpredictable release profiles.

Glipizide is one of many poorly water-soluble drugs. According to the 2002 edition of the USP (USP25, NF20), glipizide is considered practically insoluble in water (solubility is in the range of 23 µg/ml). The solubility of glipizide is a limiting factor in its ability to be delivered from an osmotic drug delivery system.

Thombre et al., (U.S. Pat. No. 5,697,922) used meglumine as a solubilizing agent for glipizide. They coated meglumine with semi-permeable polymeric films to extend the release of the solubilizer from the core. They argued that non-encapsulated solubilizers would leave the core early, leaving the drug behind in unsolubilized form. This loss of solubilizer results in erratic release or no release at all. The problem with this approach is that it is very complex, because it involves coating of the solubilizing excipient in the manufacture of the tablet. This process limits its practical significance. Also, the amount of solubilizing excipient used in this approach is exceedingly high. See also, U.S. Pat. No. 5,698,220, which discloses the use of 90% meglumine (aka, N-methylglucamine) in an osmotic dosage form for delivering glipizide.

The present invention overcomes the inadequacies of the prior art by providing ways to increase the solubility of glipizide and other poorly soluble drugs so that they can be delivered to a mammal in a safe and more effective manner. Moreover, the present invention will assist in the delivery of other compounds that have higher aqueous solubilities, but which suffer from erratic delivery from an osmotic system because of high drug load, a problem that has not been addressed in the prior art. The invention is exemplified by a drug with particularly poor water solubility, glipizide, which has presented problems with the prior art technology, and which substantiates the broad utility of the present invention.

SUMMARY OF THE INVENTION

The present invention provides an alternative to solving the problem of the controlled release, osmotic delivery of pharmaceutical agents that have low aqueous solubility, or agents that have higher solubility but suffer from delivery problems due to high drug load in a dosage unit, by providing a powerful solubilizer in the formulation: meglumine. This solubilizer can optionally be used in conjunction with a high HLB surfactant, such as sodium lauryl sulfate, to give a synergistic solubility.

The present invention also provides processes of making such osmotic dosage forms containing meglumine and,

DETAILED DESCRIPTION OF THE INVENTION

The present invention is directed to an osmotic delivery system in which a poorly water-soluble (aka low aqueous solubility) drug is delivered from the dosage unit in a solubilized form, by using a solubilizing agent that will solubilize the whole desired dosage of the drug in the core prior to release. Once the drug is in solution in the core, it can be delivered at a rate determined by the rate of water permeation through a semipermeable membrane surrounding the core of an osmotic dosage form. As a result of the enhanced solubilization, the rate of drug release from this system is predictable and reproducible, as opposed to prior art osmotics in which all or most of a hydrophobic drug is delivered as a suspension or dispersion. Moreover, by releasing the drug in solution, the likelihood of a food effect is greatly diminished.

The present invention is also applicable to the osmotic delivery of therapeutic compounds that have moderate to high aqueous solubility, but suffer from solubility limitations when present in high amounts in the confined space of an osmotic core. The solubilizer(s) of the present invention will serve to assist in the rate of dissolution of such compounds.

In an osmotic system, which is an object of the present invention, the pharmaceutically active agent is released from the device through one or more passageways, which are openings that extend between the core, containing the drug, and the exterior of the dosage form. The active agent is released from the device when water being imbibed through the semipermeable wall into the core creates an equilibrium, whereby a rate determined by the permeability of the wall and the osmotic pressure gradient across the wall continuously dissolves the active agent, or a mixture of an osmotically effective compound and the agent, producing a substantially saturated solution of agent or of the compound containing agent, which solution in either instance is delivered through the passageway(s) from the device. The dosage form will thereby deliver the active agent at a controlled and reliable rate over a prolonged period of time, because the rate of dissolution of agent is larger than the rate of release of agent from the device. The release of agent from an osmotic device is controlled by the solvent influx across the semipermeable membrane. Solvent influx, in turn, is controlled by the thickness and composition of the semipermeable membrane, the surface area of the dosage unit (tablet), and the composition of the core. All these factors can be manipulated in order to achieve customized release profiles.

The present invention provides an osmotic pharmaceutical delivery system comprising: (a) a semi-permeable wall that maintains its integrity during pharmaceutical delivery and which has at least one passageway through it connecting the core with the external environment; (b) a single, homogeneous composition within said wall, which composition is in essence composed of (i) a pharmaceutically active agent (or agents) that has/have solubility limitations due to hydrophobicity or high drug load, (ii) at least one non-swelling solubilizing agent which enhances the solubility of the pharmaceutically active agent to such an extent that the drug is in complete solution before release; and (iii) at least one non-swelling osmotic agent.

Semi-Permeable Wall

The semipermeable wall of the osmotic delivery system of the present invention is composed of a polymeric material that is applied around the core using standard techniques, such as spraying, dipping, casting, coating, solvent evaporation, molding or compression coating. The polymeric material is preferably cast or sprayed onto the tablet, typically to about 2 to about 15% weight gain of the tablet. The semipermeable wall, which completely surrounds the drug-containing core, comprises a water insoluble, pharmaceutically acceptable polymer. Suitable water insoluble polymers include, for example, cellulose esters, cellulose ethers and cellulose ester ethers. Examples of such polymers include cellulose acylate, cellulose ethyl ether, cellulose diacylate, cellulose triacylate, cellulose acetate, cellulose diacetate, cellulose triacetate, mono-, di- and tricellulose alkyls, mono-, di- and tricellulose aroyls and the like. Cellulose acetate is the preferred polymer. Other suitable water insoluble polymers are disclosed in U.S. Pat. Nos. 4,765,989 and 4,077,407, which are hereby incorporated by reference, and can be synthesized by procedures described, for instance, in Encyclopedia of Polymer Science and Technology, Vol. 3, pp. 325-354 (1964), Interscience Publishers Inc., New York, N.Y.

The water insoluble polymeric materials are preferably combined with plasticizers to impart increased flexibility, durability, and stability to the semipermeable wall. Plasticizers that can be used to impart flexibility and elongation properties to the semipermeable wall include phthalate plasticizers, such as dibenzyl phthalate, dihexyl phthalate, butyl octyl phthalate, straight chain phthalates of six to eleven carbons, di-isononyl phthalte, di-isodecyl phthalate, and the like. The plasticizers also include nonphthalates such as triacetin, dioctyl azelate, epoxidized tallate, tri-isoctyl trimellitate, tri-isononyl trimellitate, sucrose acetate isobutyrate, epoxidized soybean oil, and the like. In the case of cellulose acetate, examples of suitable plasticizers are triethyl citrate (TEC), propylene glycol (PG), a mixture of TEC and PG in ratios ranging from 25% TEC/75% PG to 75% TEC/25% PG, Tween 80 or other polyoxyethylene sorbitan esters, triacetin, diethyl phthalate, polyethylene glycol, mineral oil, tributyl sebacate, and glycerol. The amount of plasticizer in the semi-permeable wall, when incorporated therein, is from about 0.01% to 20% by weight, or higher.

The semi-permeable wall of the tablet can contain one or more passageways from the core to the exterior of the dosage form for delivering the drug. The dosage form of the invention is provided with at least one exit passageway in the semi-permeable wall. The at least one passageway allows for the uniform release of drug from the core of the osmotic dosage form. The at least one passageway can be made by mechanical or laser drilling. Alternatively, the at least one passageway is formed from a substance or polymer incorporated into the semi-permeable wall, which dissolves or erodes in the fluid environment of the gastrointestinal tract. Such erodible substances are known in the pharmaceutical arts. The at least one passageway can have any shape, such as round, triangular, square, elliptical and the like. The size of an individual passageway can range from 100 microns to 1000 microns, more preferably 200 to 900 microns, and most preferably 300 to 600 microns.

Core

Within the semi-permeable wall is the core, which contains a pharmaceutically active agent that is poorly water-soluble, or that has solubility limitations due to high drug load. By "poorly water-soluble" or "low aqueous solubility" or "hydrophobic", as used in this description and claims, is meant that the solubilities in aqueous solutions for the active ingredients contemplated in the present invention are "sparingly" (30 to 100 parts solvent to dissolve 1 part solute, or active), "slightly" (100 to 1000 parts solvent to dissolve 1 part solute), "very slightly" (1000 to 10,000 parts solvent to dissolve 1 part solute) soluble, or "practically insoluble" (more than 10,000 parts solvent to dissolve 1 part solute). The present invention also encompasses drugs of such a solubility that is higher than the foregoing, but that at the desired dosage would require or benefit from the assistance of a solubilizer to deliver the drug from the dosage unit in a solubilized state at a desired rate and in the desired profile. Typically, such drugs would include those that may have moderate to high solubilities, but which require a high drug load in the dosage core. "High drug load" is used herein to mean that the dosage unit contains 30% or more of the drug.

The terms "drug" or "(pharmaceutically) active agent" or simply "active" are used in the present specification and claims to mean any compound useful for therapeutic, nutritional, or diagnostic purposes. Further, the terms encompass one or more of such poorly water-soluble compounds, or one or more of such compounds in composition with any other active agent(s). Additionally, the present invention is intended as useful for the delivery of such agents to any animal, but preferably mammals, and most preferably humans.

The present invention is not limited to only certain active agents, but is for example applicable to any poorly water-soluble compound for which controlled release delivery is desired. Non-limiting examples of such active agents would include albendazole, albuterol, acyclovir, adriamycin, carbamazepine, oxcarbazepine, amiodarone, amlodipine, amphetamine, amphotericin B, atorvastatin, atovaquone, azithromycin, baclofen, bicalutamide, busulfan, butenafine, calcipotriene, calcitriol, camptothecin, capsaicin, carotenes, celecoxib, cerivastatin, chlorpheniramine, cimetidine, ciprofloxacin, cisapride, cetirizine, clarithromycin, clemastine, codeine, cyclosporin, danazol, dantrolene, dexchlorpheniramine, digoxin, dirithromycin, donepezil, efavirenz, ergotamine, etodolac, etoposide, famotidine, fentanyl, finasteride, fluconazole, flurbiprofen, fluvastatin, fosphenyloin, frovatriptan, gabapentin, gemfibrozil, glibenclamide, glyburide, glimepiride, griseofulvin, halofantrine, ibuprofen, irinotecan, isotretinoin, itraconazole, ivermectin, ketoconazole, ketorolac, lamotrigine, angiotensin converting enzyme (ACE) or NEP inhibitors, fenofibrate, fexofenadine, flutamide, glipizide, glyburide, isradipine, loratadine, lovastatin, melphalan, nifedipine, leflunomide, loperamide, lycopenes, mifepristone, mefloquine, methadone, methoxsalen, metronidazole, miconazole, midazolam, miglitol, mitoxantrone, nabumetone, nalbuphine, naratriptan, nelfinavir, nilutamide, nizatidine, oxaprozin, paclitaxel, pentazocine, pioglitazone, pizotefin, pravastatin, probucol, pyridostigmine, raloxifene, rofecoxib, repaglinide, rifapentine, rimexolone, rizatriptan, rosiglitazone, saquinavir, sibutramine, sildenafil citrate, simvastatin, sirolimus, spironolactone, sumatriptan, tacrine, tacrolimus, tamoxifen, tamsulosin, targretin, tazarotene, teniposide, terbinafine, tiagabine, tizanidine, topiramate, topotecan, toremifene, tramadol, tretinoin, troglitazone, trovafloxacin, verteporfin, vigabatrin, vitamin A, vitamin D, vitamin E, vitamin K, zafirlukast, zileuton, zolmitriptan, zolpidem, zopiclone, proton pump inhibitors such as lansoprazole, esomeprazole, omeprazole, and rabeprazole, MAP kinase inhibitors, ICE inhibitors such as pralnacasan, pseudoephedrine, indomethacin, naproxen, estrogens, testosterones, steroids, phenyloin, ergotamines and cannabinoids, pharmaceutically acceptable salts, isomers, prodrugs (e.g. esters) and derivatives thereof, and mixtures thereof.

Preferred hydrophobic actives include albuterol, acyclovir, adriamycin, carbamazepine, oxcarbazepine, cyclosporin, griseofulvin, angiotensin converting enzyme (ACE) or NEP inhibitors, fenofibrate, fexofenadine flutamide, glipizide, glyburide, isradipine, loratadine, lovastatin, melphalan, nifedipine, proton pump inhibitors, MAP kinase inhibitors, pralnacasan, pseudoephedrine, indomethacin, naproxen, estrogens, testosterones, steroids, phenyloin, sumatriptan, ergotamines or cannabinoids, or pharmaceutically acceptable salts, isomers, or prodrugs or derivatives thereof. More preferred are those selected from carbamazepine, oxcarbazepine, fenofibrate, fexofenadine, glipizide, lorsoprasole, esomeprazole and rabeprozole, or pharmaceutically acceptable salts, isomers, or prodrugs or derivatives thereof. Glipizide is particularly exemplified in the examples herein, but is merely representative of any other such drugs with solubility barriers. Particular, but non-limiting, examples of drugs that are high dose (100 mg or higher per dosage unit) with moderate to high solubility and that will benefit from the solubilizer(s) in the present osmotic system include diltiazem HCl, verapamil HCl, metoprolol succinate, quetiapine fumarate, valganciclovir HCl, theophylline, and naproxene sodium.

The concentration of drug in the core depends, of course, on the desired dosage of the active agent. It will be appreciated that the amount of a compound of the invention required for use in treatment will vary not only with the particular compound selected but also the nature of the condition for which treatment is required, and the desired dosage regimen, it being understood that extended or sustained release dosage forms such as those of the instant invention are usually intended to reduce the number of dosages taken per day or to sustain a desired plasma level. Additionally, the necessity or desire for other components of the dosage core will serve to dictate the maximum percentage of drug. In general, however, the core of a dosage unit according to the present invention will contain anywhere from about 0.5% by weight to about 90% by weight of the core, preferably from about 1 to about 50%, and more preferably from about 1 to about 10%. Glipizide, for instance, is present in this system in an amount of from about 0.5 wt. % to about 5.0 wt. %, preferably from about 1.0 wt. % to about 3.0 wt. %, and most preferably about 2.5%.

At the heart of this invention is the discovery that a powerful solubilizing agent can be used in an osmotic system to enhance the solubility of the pharmaceutically active agent that has low aqueous solubility or other solubility limitations, and which is included in the composition of the core at a pharmaceutically reasonable amount. Solubilizing agents previously used in osmotic tablets, for example those containing glipizide, resulted only in partial solubilization of the active drug during oral drug delivery, leaving most of the active in the core in an unsolubilized state. Sodium lauryl sulfate (SLS) was originally used as a solubilizer for glipizide (U.S. Pat. Nos. 6,361,796 and 6,514,532). A solution containing SLS at a concentration of 100 mg/mL can solubilize 2.44 mg/mL of glipizide.

In the formulas disclosed in Example 5 of U.S. Pat. Nos. 6,361,796 and 6,514,532, mentioned in the Background section herein, the concentration of SLS used is 78.6 mg/mL, and the concentration of glipizide (total) is 35.7 mg/mL. As noted above, a pure solution of SLS at 100 mg/mL can only dissolve 2.44 mg/mL of glipizide. Given that there was only 78.6 mg/mL of SLS in the core of the formulas of said prior patents, it would not have been possible to solubilize 35.7 mg/mL of glipizide per tablet. This limitation in the solubilizing capacity of prior solubilizers may well result in erratic and unpredictable dissolution profiles.

In the new osmotic system of the present invention, meglumine, alone or in combination with high HLB (greater than or equal to 15) anionic or non-ionic surfactant(s), significantly enhances the solubility of hydrophobic compounds in the core, resulting in predictable and consistent release profiles. Examples of high HLB anionic surfactants include, for example, alkyl sulfates (such as sodium lauryl sulfate), alkyl aryl sulfonates, and long alkyl-chain sulfonates (such as sodium bis-(2-ethylhexyl)sulfosuccinate, aka sodium docusate). High HLB non-ionic surfactants include, for example, polyethylene oxide-polypropylene oxide-polyethylene oxide triblock co-polymers (available under the trade name of Lutrol® from BASF Corporation), and polysorbates.

As an example of the capabilities of the present invention, with meglumine, and optionally SLS, it is now possible to achieve a solution containing up to 70 mg/mL of glipizide. This results in the solubilization of an active amount of glipizide in the core prior to its release from the dosage unit, such that the drug is released from the core to the exterior of the dosage unit as a solution for the most part, and not a suspension or dispersion. Meglumine can be used in amounts preferably ranging from 1% by weight to 10% by weight of the core, and more preferably from 4% by weight to 6% by weight. As a most preferred embodiment, 5% by weight meglumine is used in the core compositions.

Sodium lauryl sulfate can be used at concentrations ranging from 0% to 10% by weight of the core. The preferred sodium lauryl sulfate concentration is from 4% to 6% by weight.

The core also contains at least one non-swelling osmotic agent. Examples of non-swelling osmotic agents include, but are not limited to, xylitol, mannitol, sorbitol, inositol, sucrose, lactose, dextrose, maltodextrins, and salts, such as sodium chloride for instance. In general, the at least one non-swelling osmotic agent is present in the system in an amount of from about 10% to about 99% of the core, depending on inter alia the drug load. For hydrophobic active agents, the amount is preferably 60 wt. % to about 99 wt. %, and more preferably from about 80 wt. % to about 95 wt. %.

Crystallization inhibitors such as low molecular weight polyvinylpyrrolidone, polyethylene glycol, cyclodextrins, gelatin, maltodextrin, sorbitol, and polyglyceryl mixed vegetable fatty acid esters may also be used in combination with meglumine to foster the solubility of glipizide or other actives that have a tendency to crystallize. Crystallization inhibitors, if present, are typically added in an amount of up to about 10% by weight of the core, preferably up to about 5%.

Optionally, but preferably, the core composition can contain one or more lubricants, which may be added to assure proper tableting. Non-limiting examples of lubricants include magnesium stearate, calcium stearate, zinc stearate, stearic acid, polyethylene glycol, leucine, glyceryl behenate, sodium lauryl sulfate, sodium stearyl fumarate, hydrogenated vegetable oils, and other waxes, including but not limited to, beeswax, carnuba wax, cetyl alcohol, glyceryl stearate, glyceryl palmitate, and stearyl alcohol. The lubricant, when present, is typically in an amount of from about 0.1 wt. % to about 20 wt. % of the core, preferably from about 1 to about 10% wt. %, and more preferably about 0.3 to about 3.0 wt. % (or "w/w").

In addition, the core composition may contain one or more binders to give the core tablets cohesiveness. Such binders are well known in the art, and include such substances as polyvinyl pyrrolidone, starch, Maltrin, methylcellulose, hydroxypropyl methylcellulose, carboxymethyl cellulose, sucrose solution, dextrose solution, acacia, tragacanth and locust bean gum, which may be applied wet. The binding agent may be present in the core composition in an amount of from about 0.2 wt. % to about 20 wt. %, preferably from about 5 wt. % to about 15 wt. %.

As a further embodiment, the core may take the form of a matrix tablet in customizing the desired profile. In general, any inert polymeric matrix can be used to form the tablet core of the present osmotic system, provided of course that the tablet includes the required meglumine described herein. If dealing with a highly soluble drug, the hydrophobic matrix dosage form as described in U.S. Pat. No. 5,484,608, incorporated herein by reference, may be used as the core of the osmotic dosage unit of the present invention, for example, which would further include meglumine as well as other optional components such as SLS.

Furthermore, any core of the present invention may also be multilayered (typically, double or triple layered). Such tablets can comprise layers of different composition, such as different drugs and/or matrix or not, with one, two or all layers containing the solubilizer(s) according to the present invention. Such bi- or tri-layered tablet cores are useful to further tailor the profile, such as to achieve pulsitile release, or to include in one dosage unit drugs of different compatibilities or release profiles.

The tablet cores (indeed, the osmotic dosage unit as a whole) can be of any shape and reasonable size.

In a preferred embodiment, the system may further include an overcoat that covers the semi-permeable wall. The overcoat may provide a layer of a water-soluble pharmaceutically active agent on the exterior of the semi-permeable membrane. In such systems, the pharmaceutically active agent that is exterior to the semi-permeable membrane is released quickly to provide a quick and initial relief of symptoms to a patient. This initial release of the pharmaceutically active agent is of an immediate release type of profile. After the release of the pharmaceutically active agent that is exterior to the semipermeable membrane, the pharmaceutically active agent in the core portion is released at a rate that is preferably zero order, although non-zero release is not excluded hereby. See, e.g., U.S. Pat. No. 4,801,461, which is hereby incorporated by reference.

Alternatively, the overcoat can be formulated to provide light protection, atmospheric humidity protection, and/or a brief lag time in the release of the insoluble active agent from the osmotic delivery system. The overcoat may also be used to provide a pharmaceutically elegant finish to the dosage form. The overcoat may comprise a mixture of a sustained release polymer, such as ethylcellulose, and a water-soluble polymer such as hydroxypropylcellulose to act as a pore-former. The overcoat is applied by standard methods onto the tablets, such as by casting, compression coating, electrostatically depositing or spraying, typically to about 2% to about 15% weight gain of the tablet. The ratio of sustained release polymer to water-soluble polymer is varied to achieve the desired lag time, humidity protection, and/or light protection. The ratio of sustained release polymer to water-soluble polymer may vary from 9:1 to 1:9, but is preferably from 1:1 to 9:1, and more preferably from 3:1 to 5:1. In general, a higher water-insoluble to water-soluble polymer ratio results in slower drug release and an extended lag time. In such systems, the contribution of the overcoat to overall drug release rate is significant. However, in systems with a higher proportion of water-soluble polymers, the contribution of the overcoat to drug release rate becomes less significant.

Core Preparation

The core composition containing the active agent or agents in accordance with the present invention may be prepared for tablet compression by any of several standard techniques known to those skilled in the art. Such methods include, but are not limited to, fluid bed granulation, dry granulation, direct compression, roller compaction, and wet granulation with aqueous or solvent based binders. Other, or supplementary, methods can be found, inter alia, in Remington's Pharmaceutical Sciences, 18$^{th}$ Edition, Mack Publishing, Pennsylvania, 1990, ISBN 0-912734-04-3, particularly Chapters 89 and 91 thereof, the entirety of which is hereby incorporated herein by reference.

A preferred method herein is wet granulation, which can be performed using a high shear granulator or a fluid bed granulator. Fluid bed granulation is preferred. With this method, the active agent or agents are mixed with, at least, meglumine, and a binder solution and sprayed to form granules. The granules are dried in the fluid bed and then dry screened. Once granulation is achieved, the granules can be lubricated by adding magnesium stearate or other suitable tablet lubricating agents, which is followed by dry blending in a tumble blender or other suitable mixer to effect adequate distribution of the tablet lubrication agents. The lubricated granules then are compressed on a rotary tablet press. The tablets must have sufficient hardness and acceptable friability to allow for coating.

Matrix tablets, as well, can be prepared by any method known in the art, with the exception that the solubilizer(s) is/are included in the mixture prior to compressing. In general, the components of the core are dry-mixed and then compressed into tablets. If the matrix is of a waxy material, typically the active(s) and the solubilizers(s) in addition to any other desired components are dispersed in molten wax, congealed and granulated prior to compression into tablets.

Multilayered tablets are, in general, prepared by compressing another granulation or mixture upon an already compressed or partially compressed core prepared in accordance with the present invention, which compression can be repeated if desired. In the system of the present invention, at least one layer contains the solubilizer(s).

Coating of Core

The core tablets, obtained by any of the foregoing methods or others known in the art, are then coated with a semi-permeable film, which forms the semi-permeable wall described above in this description. The tablets can be coated by any means and methods known now or later; preferred methods of coating include pan coating, Wurster column coating, compression coating and electrostatic deposition. The coating solution or coating formulation is prepared and applied at a rate that will preferably provide a smooth and even coverage of the entire surface area of the tablet. The percent weight gain of the tablet as a result of application of the coating will vary, depending upon the size and shape of the tablet that is coated, but generally is from about 2% to about 15%.

A passageway is then formed in the semi-permeable film coated tablets by laser drilling, mechanical drilling, or other drilling methods known to those skilled in the art. Other methods of forming a passageway or a multiplicity of passageways also are known to those skilled in the art, such as erosion of a water-soluble component that has been blended with the water-insoluble polymer to form part of the semi-permeable wall.

When an overcoat is applied to the semi-permeable film coated tablet, the overcoat preferably is applied in a pan coater or a Wurster fluidized bed column coater, although any known coating process or apparatus can be used. The coating solution is applied such that it will provide a smooth and even coverage over the entire surface area of the tablets. The coating solution may be an aqueous solution or a solvent based solution. The percent weight gain provided by the overcoat will vary, depending upon the size and shape of the tablets, but generally is from about 2% to about 15%.

Administration and Treatment

The present invention further provides a method of administering a dosage form of the present invention to an animal, preferably a human. It is primarily contemplated that the dosage forms described herein are administered by an oral route. The desired dose may conveniently be presented in a single dose or as divided dose administered at appropriate intervals, for example as two, three, four or more doses per day. However, it is contemplated that the administration of the dosage forms will provide for a decreased dosage regimen, for instance a once daily dosage as opposed to two or more daily dosages. That is, the dosage forms of the present invention are of a sustained (zero order) release, which can be manipulated in the manner described above to attain, for example, immediate release followed by a zero, first order or other non-zero order release profile. Most preferably, the dosage units of the present invention provide for a once-daily dosing regimen of the active agent(s).

Moreover, the dosage forms of the present invention may be customized to provide for the immediate release of a first active agent, followed by the zero or non-zero order release of a second active. Such dosage forms are useful to obtain an immediate relief of symptoms, followed by sustained control of symptoms. For example, an analgesic can be coated on the outside of the dosage unit, as well as the same or another analgesic in the core. Or, a drug such as loratidine can be coated on the outside of the osmotic for immediate release, with pseudoephedrine in the core for extended allergy relief. Numerous other combinations are possible.

Furthermore, the dosage unit of the present invention may be of an "osmotic within an osmotic" form, such as is described in U.S. Pat. Nos. 6,004,582 and 6,491,949, or of a core of concentrical layers that contain different concentrations of a drug or different drugs.

The osmotic dosage forms of the present invention are used to treat an abnormal condition, provide nutritional supplementation, and/or deliver diagnostic agents to a mammal, preferably human, in need thereof. Basically, the method of treating such a condition involves orally administering a dosage form of the present invention to the subject in need of treatment. It is likely that due to the controlled release of active(s) in accordance with the present invention, there is a reduction in the number and severity of side effects normally associated with the active(s) being delivered. The terms "treat", "treating" and "treatment" are intended to include prevention of a condition or illness as well.

As a preferred embodiment, osmotic dosage forms of the present invention that contain glipizide as an active ingredient can be used to treat hyperglycemic conditions in patients in a manner known in the art.

It will be appreciated by those skilled in the art that the active ingredients can be used in the form of pharmaceutically acceptable salts, free bases, prodrugs (e.g. esters) or derivatives and, in the case of chirally active ingredients, one can use one or both optical isomers, geometric isomers and mixtures thereof including racemic mixtures.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention now will be described in particularity with the following illustrative examples; however, the scope of the present invention is not intended to be, and shall not be, limited to the exemplified embodiments below.

EXAMPLES

Example 1

Solubility Studies

Solubility studies were undertaken to examine the effect of solubilizers on glipizide. Samples were prepared using either meglumine or sodium lauryl sulfate (SLS).

One percent, 5%, and 10% solutions of meglumine were prepared. Glipizide was added to each vial of the meglumine solution until the solution was saturated with respect to glipizide (see Table 1).

The samples were placed on a mechanical rotator for approximately 24 hours. The samples were filtered with 0.2 um Acrodisc® filters.

One percent, 5% and 10% solutions of SLS were prepared in the same way as the meglumine solutions, above. Table 2 provides the composition of these solutions. Solubility studies were carried out in the same manner as those with meglumine.

TABLE 1

Glipizide solubility samples containing meglumine as a solubilizer

| Percent Solution | Amount of Meglumine (g) | Amount of water (g) | Amount of Glipizide (mg) |
|---|---|---|---|
| 1% | 0.11 | 10.01 | 450 |
| 5% | 0.51 | 10.47 | 600 |
| 10% | 1.00 | 10.01 | 750 |

TABLE 2

Glipizide solubility samples containing sodium lauryl sulfate (SLS) as a solubilizer

| Percent Solution | Amount of SLS (g) | Amount of water (g) | Amount of Glipizide (mg) |
|---|---|---|---|
| 1% | 0.11 | 10.00 | 149.6 |
| 5% | 0.53 | 10.04 | 150.5 |
| 10% | 1.07 | 10.02 | 149.8 |

Finally, a combination of meglumine and SLS was also examined. This composite formula contained 2% SLS and 5% meglumine. Approximately 857 mg of glipizide was added to make a saturated solution. Table 3 provides the solubility results.

TABLE 3

Glipizide's saturation solubility in the presence of solubilizers

| Sample | Solubility (mg/mL) |
|---|---|
| 1% meglumine | 16.14 |
| 5% meglumine | 55.40 |
| 10% meglumine | 108.77 |
| 1% SLS | 0.34 |
| 5% SLS | 1.49 |
| 10% SLS | 2.44 |
| 2% SLS, 5% meglumine | 72.83 |
| Glipizide (control) | 0.028 |

Example 2

Formulation

Based on the solubility results in Example 1, (1) meglumine and (2) meglumine plus sodium lauryl sulfate (SLS) containing formulas were prepared (Tables 4 and 5).

TABLE 4

Formula containing meglumine

| Material | % |
|---|---|
| Glipizide | 2.24 |
| Xylitol CM90** | 44.45 |
| Maltrin ® M150* (wet) | 1.31 |
| Maltrin ® M150* (dry) | 45.09 |
| Meglumine | 4.94 |
| Magnesium Stearate | 0.98 |
| Stearic Acid | 0.98 |

*Maltrin ® M150 Maltodextrins available from Grain Processing Corp., Muscatine, Iowa.
**Xylitol, crystalline powder, available from Cultor Food Science of Ardsley, N.Y.

TABLE 5

Formula containing meglumine and SLS

| Material | Weight % |
|---|---|
| Glipizide | 2.27 |
| Xylitol CM90 | 45 |
| Maltrin ® M150 (wet) | 1.33 |
| Maltrin ® M150 (dry) | 39.4 |
| Meglumine | 5 |
| SLS | 5 |
| Magnesium Stearate | 1 |
| Stearic Acid | 1 |

Both formulas were granulated using a GPCG-1 Glatt fluid bed (Glatt Air Techniques, Ramsey, N.J.). Glipizide, xylitol CM90, Maltrin M150, and meglumine were added to the fluid bed granulator and granulated by spraying Maltrin M150 solution (Maltrin wet) as a granulating fluid (binder). In formulas where SLS is used in combination with meglumine, both SLS and meglumine were added to the fluid bed granulator with the rest of the components and granulated by spraying Maltrin solution. Granules were dried in the fluid bed granulator to a moisture level of below 3%. Dry granules were screened to remove aggregates. The granules obtained were blended in a V-blender with stearic acid for 5 minutes, and then magnesium stearate was added and blended for an additional 3 minutes. The blend was tableted on a Kilian Press (Kilian and Co. Inc., Horsham, Pa.) using ⅜" round standard concave tooling.

The tablets were either coated with a triethylcitrate plasticized cellulose acetate (TEC/CA) or a polyethylene glycol plasticized cellulose acetate (PEG/CA) coating system for the semi-permeable wall. The cellulose acetate coating system contains cellulose acetate and a plasticizer (triethylcitrate or polyethylene glycol as a plasticizer) dissolved in acetone (in the case of TEC) and a mixture of acetone and water (9:1) (in the case of PEG). The coating was applied on the tablets using a pan coater. The amount of coating polymer applied onto the tablets is described in terms of weight gain by the tablet. The coated tablets were laser drilled with a single hole having a diameter of approximately 386-405 µm.

Figure 1:
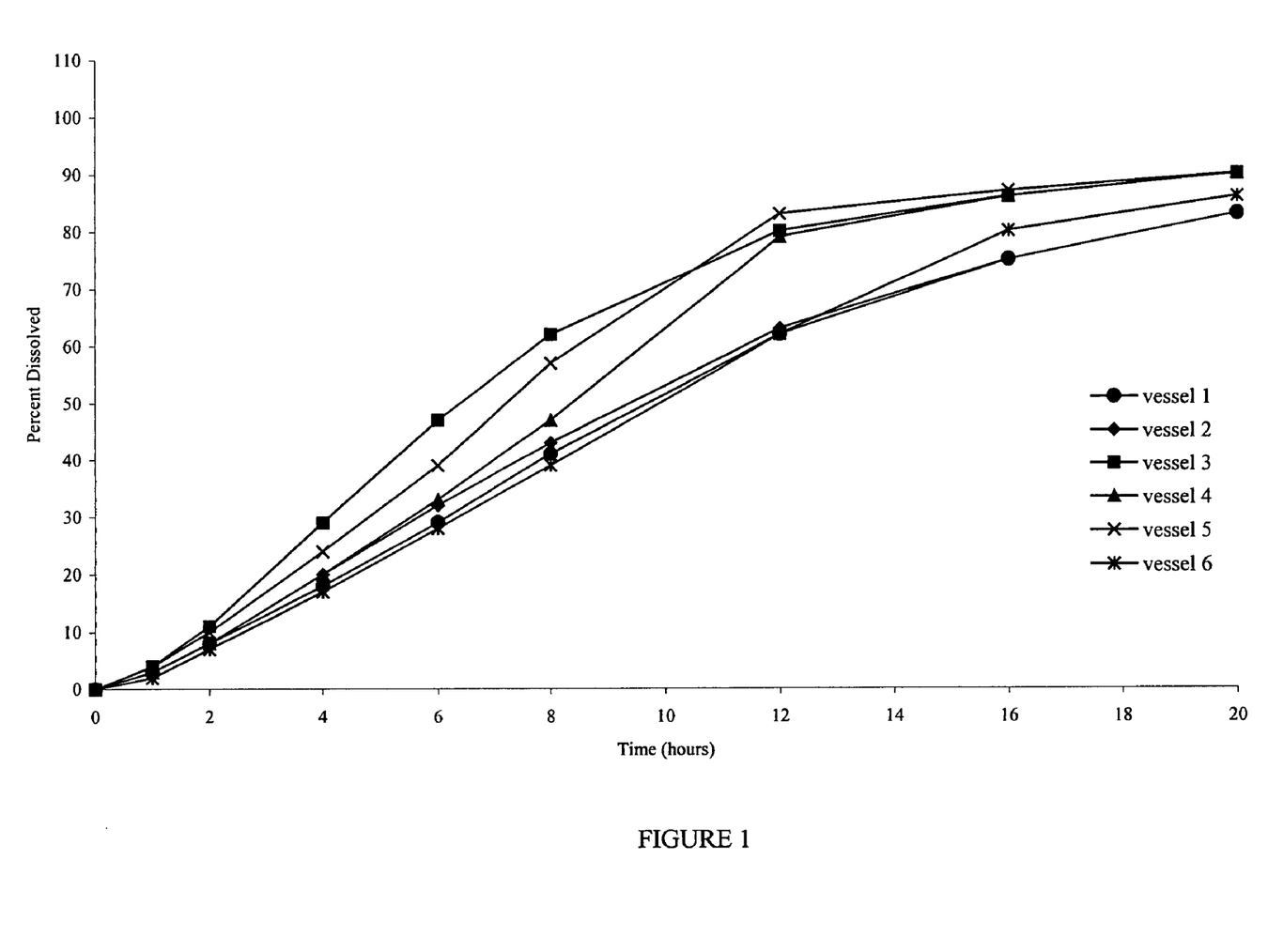
FIG. 1 shows the dissolution profile for glipizide osmotic tablets containing 5% meglumine in the core with a 3% weight gain 20% TEC/80% CA coating made in accordance with the present invention.

FIG. 1 shows the dissolution profile for glipizide osmotic tablets containing 5% meglumine in the core coated with a 20% TEC/80% CA coating to a 3% weight gain.

Figure 2:
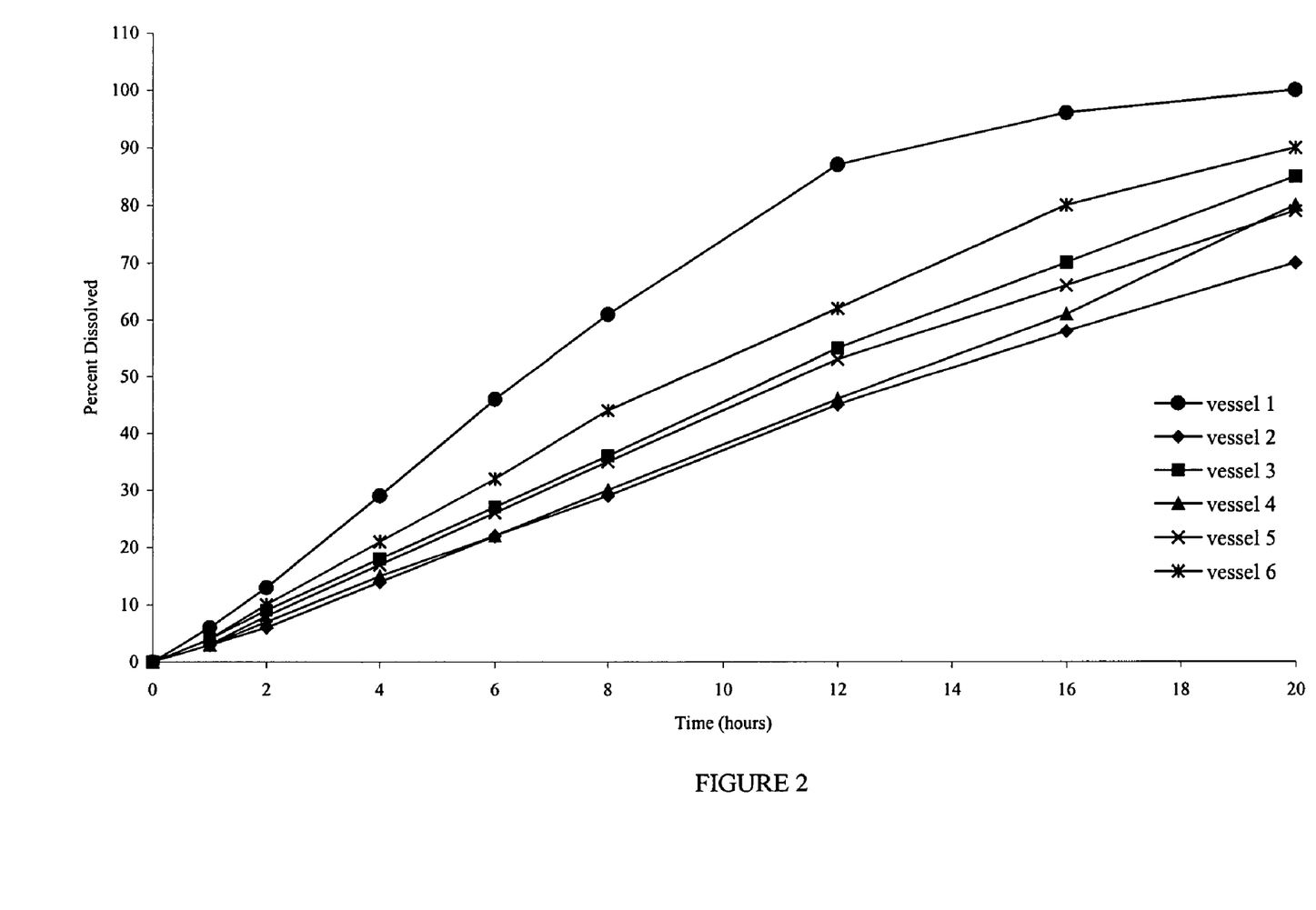
FIG. 2 presents the dissolution profiles for a formula containing 5% meglumine and 5% sodium lauryl sulfate with a 20% TEC/80% CA coating to a weight gain of 3%.

The results in FIG. 1 show the dissolution profiles for 5% meglumine in the formula, coated to 3% weight gain with a coating system composed of 20% TEC/80% CA. Shown in FIG. 2 are the dissolution profiles for a formula containing 5% meglumine and 5% sodium lauryl sulfate with the 20% TEC/80% CA coating, also to a weight gain of 3%. FIGS. 1 and 2 show comparable dissolution profiles. The advantage of adding SLS to the core in this instance is not readily apparent, because the drug concentration that is achieved if all goes into solution is 35.7 mg/l. As shown in Table 3, meglumine alone and meglumine plus SLS are capable of solubilizing much more glipizide. The release rates in both cases meet the in vitro requirement for a once daily administration of glipizide.

Figure 3:
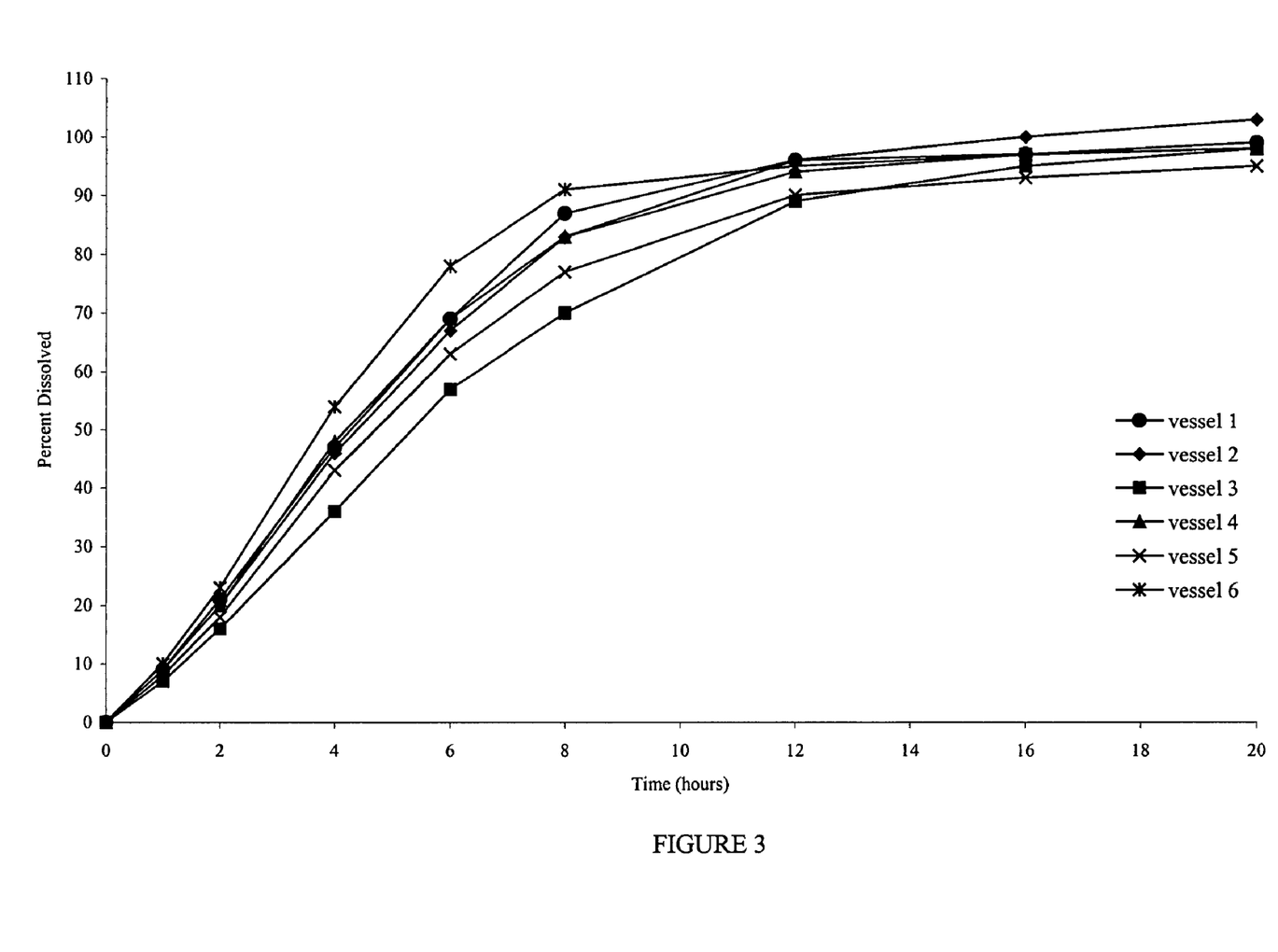
FIG. 3 shows the dissolution profiles for the meglumine/SLS containing cores coated to a 2% weight gain using 20% TEC/80% CA.
Figure 4:
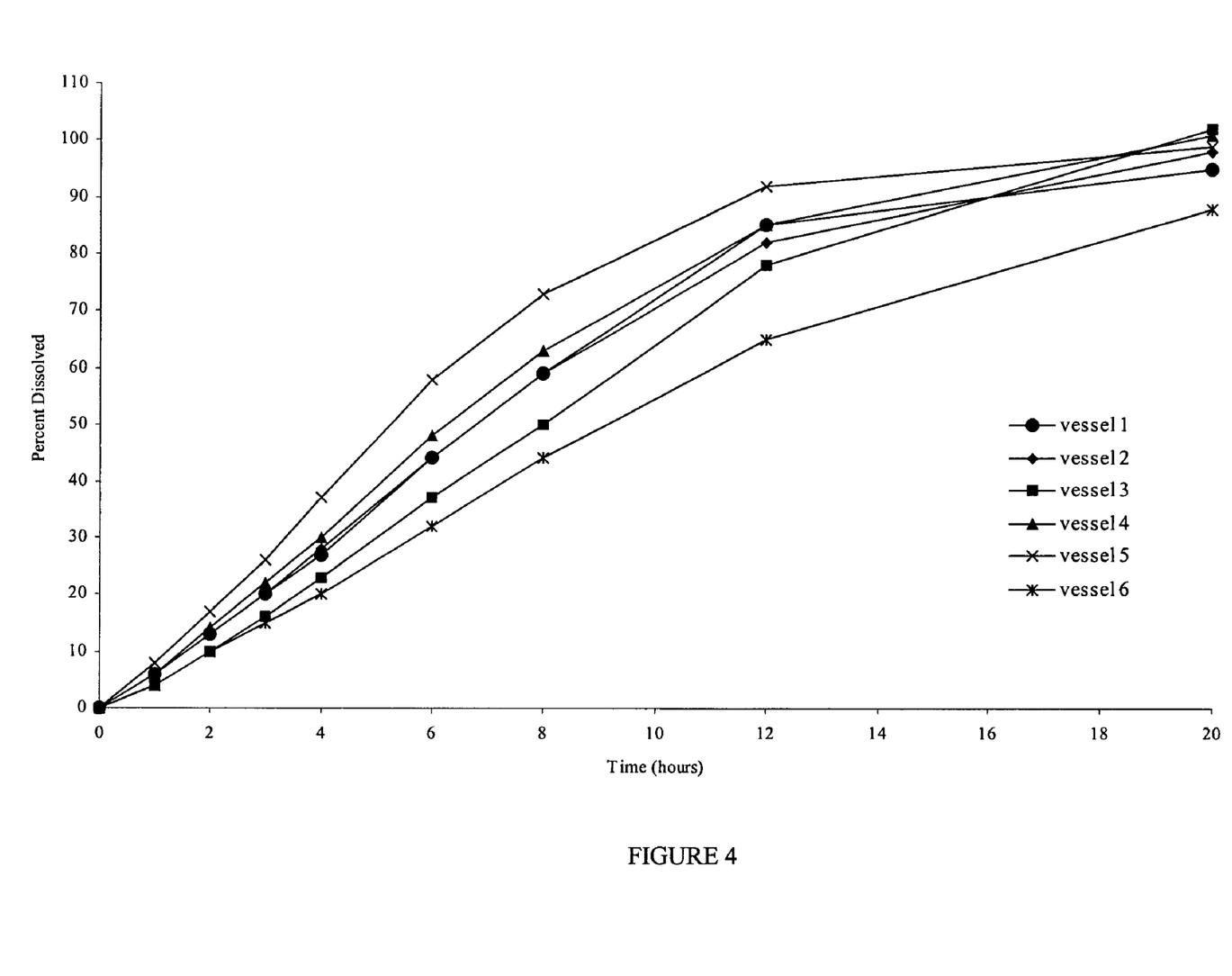
FIG. 4 show the dissolution profiles for the meglumine/SLS containing cores coated to a 2.5% weight gain using 20% TEC/80% CA.

FIGS. 3 and 4 show the dissolution profiles for the meglumine/SLS containing cores coated to 2% and 2.5% weight gains, respectively, using the 20% TEC/80% CA coating system. An increase in the coating thickness slowed down the release of glipizide. The profiles for the 2% weight gain were fast and hence do not meet the in vitro requirement for a once daily administration of glipizide. However, the increase in coating level from 2% to 2.5% weight gain slowed the release rate enough to meet the in vitro requirement for once daily administration.

Figure 5:
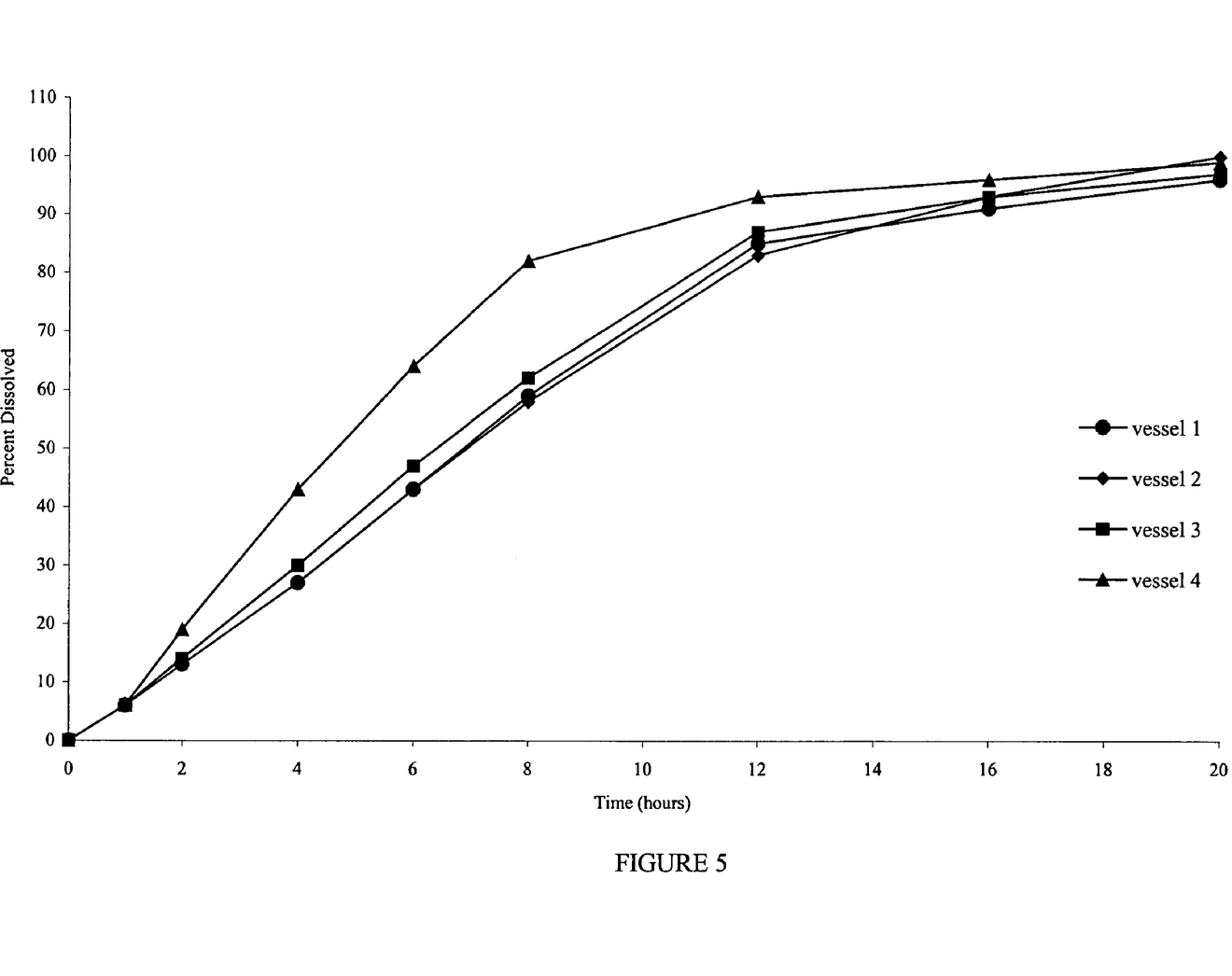
FIG. 5 shows a dissolution profile for a glipizide tablet containing meglumine/SLS, which is coated to a 2.5% TEC/CA weight gain, wherein the dissolution method is a "basket over paddle" method.

FIG. 5 shows a dissolution profile for the glipizide tablet containing meglumine/SLS and coated to 2.5% TEC/CA weight gain using a basket over paddle dissolution method. In this modified method, the dosage unit sits in a stationary basket and the paddle stirs the dissolution medium. Whereas all the earlier dissolution profiles were carried out using a USP standard basket method (USP Apparatus I), this prototype was tested using this modified dissolution method. This alternative method resulted in similar profile as the one using the USP apparatus 1, indicating the robustness of the formulation.

Example 3

Dissolution Variations

Also examined was the dissolution behavior of the meglumine/SLS containing core in a medium that simulates the gastrointestinal tract (GIT) fluid. Dissolution was carried out in simulated gastric fluid (SGF) for the first two hours, followed by simulated intestinal fluid (SIF) for the remainder of the time (18 Hrs). A simulated gastric fluid is composed of 2.0 gm sodium chloride, 3.2 gm purified pepsin in 7.0 ml of hydrochloric acid and sufficient quantity of water to make 1000 ml. The pH of the resulting solution is approximately 1.2. A simulated intestinal fluid is composed of 6.8 gm monobasic potassium phosphate, 0.62 gm sodium hydroxide, and 10 gm pancreatin. The pH of the resulting solution is adjusted to 6.8.

Figure 6:
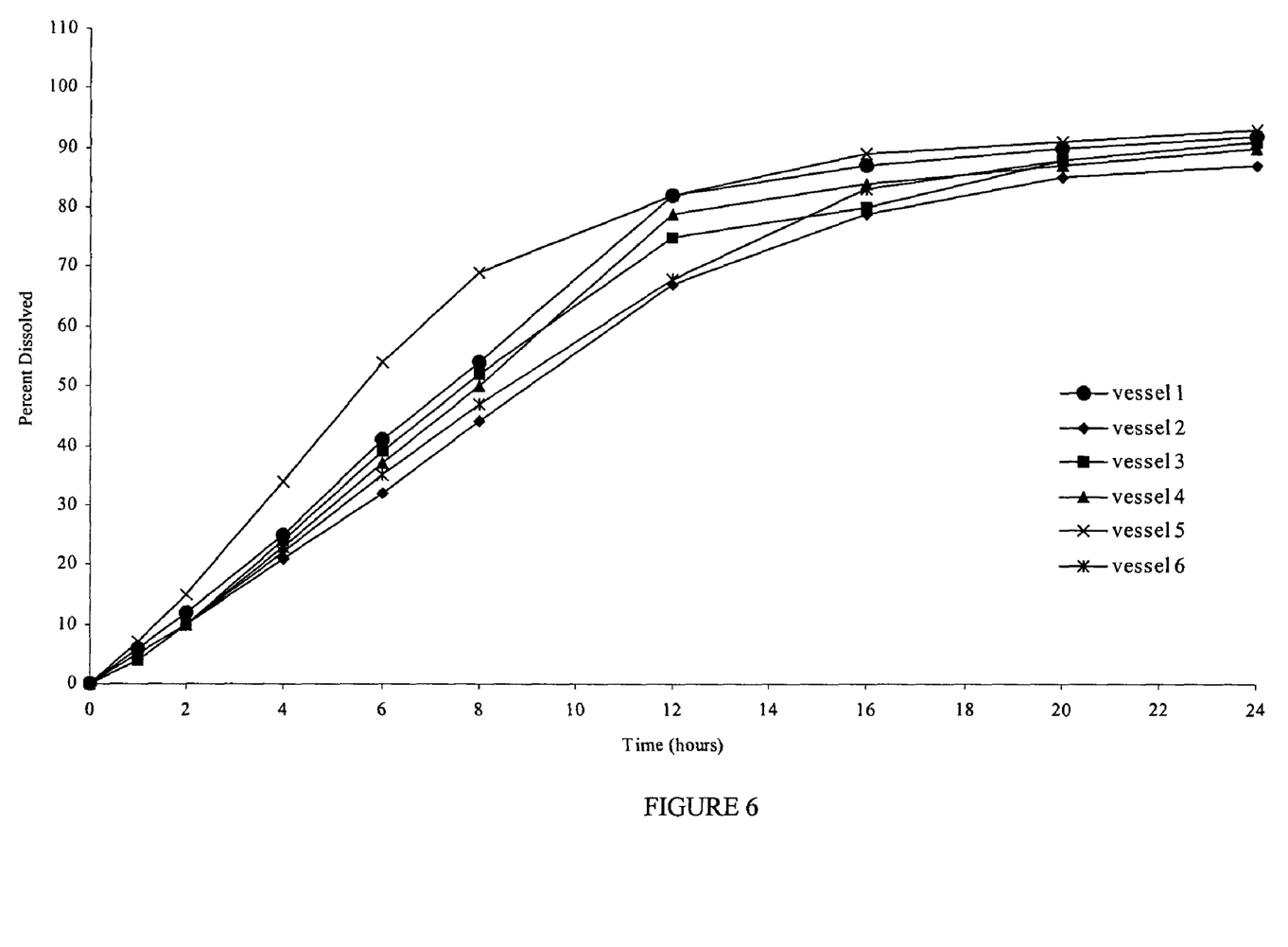
FIG. 6 shows dissolution profiles of certain formulations made in accordance with the present invention, as set forth in the examples, wherein the dissolutions are conducted in simulated gastric and intestinal fluids as the dissolution media.

FIG. 6 shows the dissolution profiles in the simulated gastric and intestinal fluids as the dissolution media.

Figure 7:
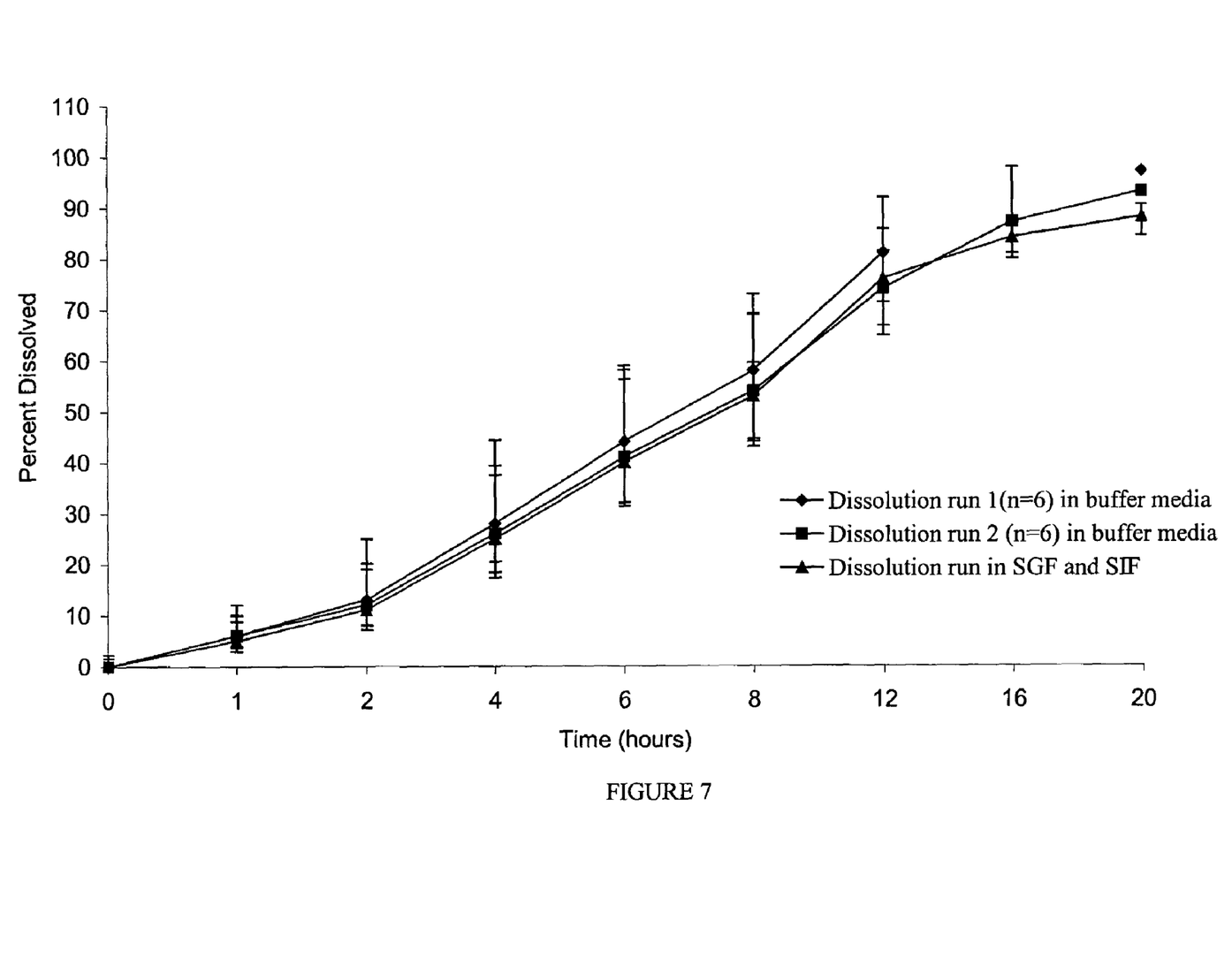
FIG. 7 shows a comparison of the dissolution profiles in different media.

FIG. 7 shows that the dissolution profiles are comparable, and reproducible, irrespective of the type of media used.

Example 4

Coating Systems

A different coating system was also tried on the meglumine and SLS containing glipizide tablets. In this coating system, the plasticizer used was polyethylene glycol 3350 (Carbowax™, Dow Chemical Co., Midland, Mich.). The coating system is composed of 7% by weight of polyethylene glycol 3350 and 93% by weight of cellulose acetate. Tablets were coated to 3%, 4% or 5% weight gain.

Figure 8:
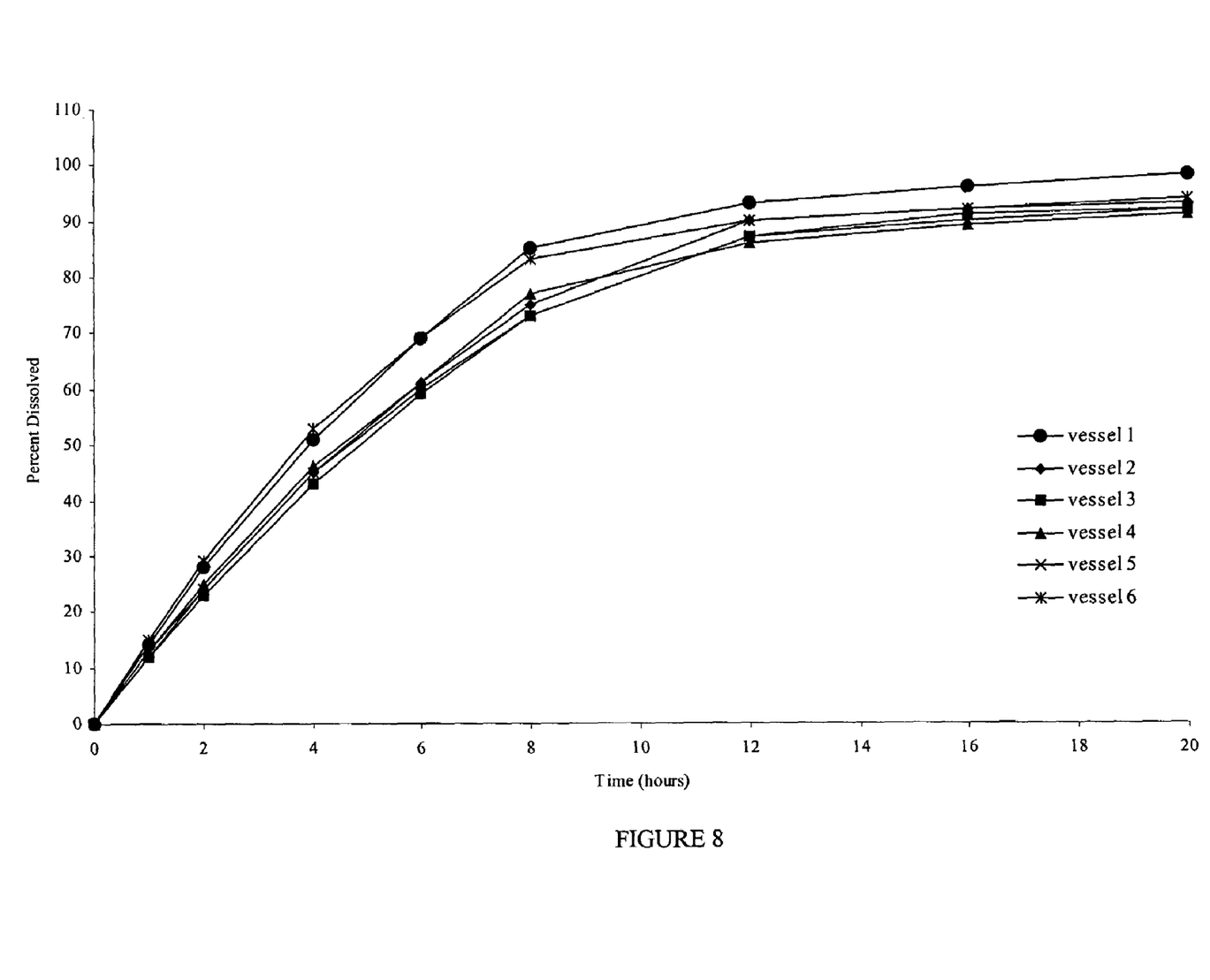
FIGS. 8, 9 and 10 present the dissolution profiles of tablets coated to 3%, 4%, or 5% weight gain with a coating composed of 7% by weight of polyethylene glycol 3350 and 93% by weight of cellulose acetate.
Figure 9:
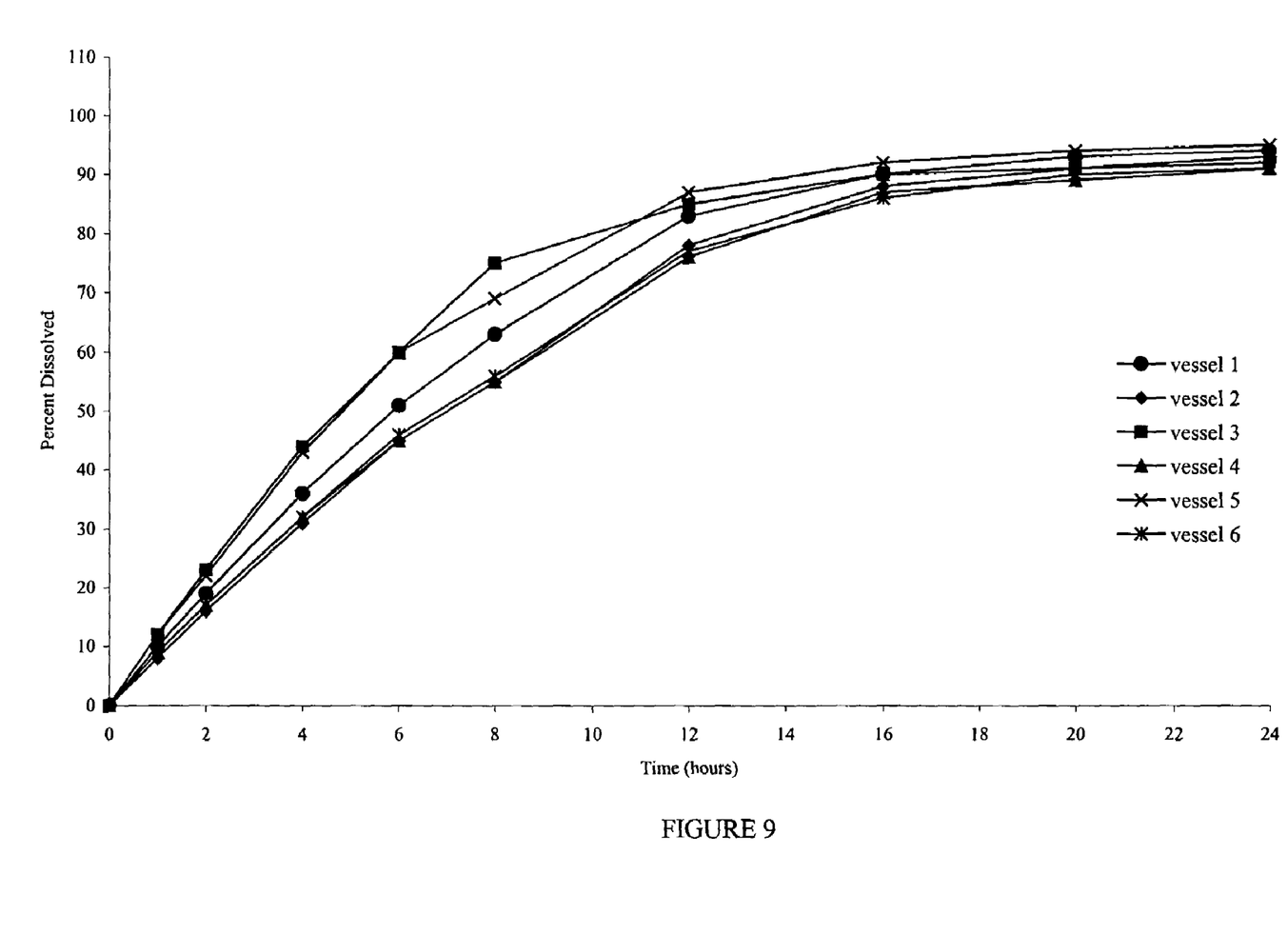
Figure 10:
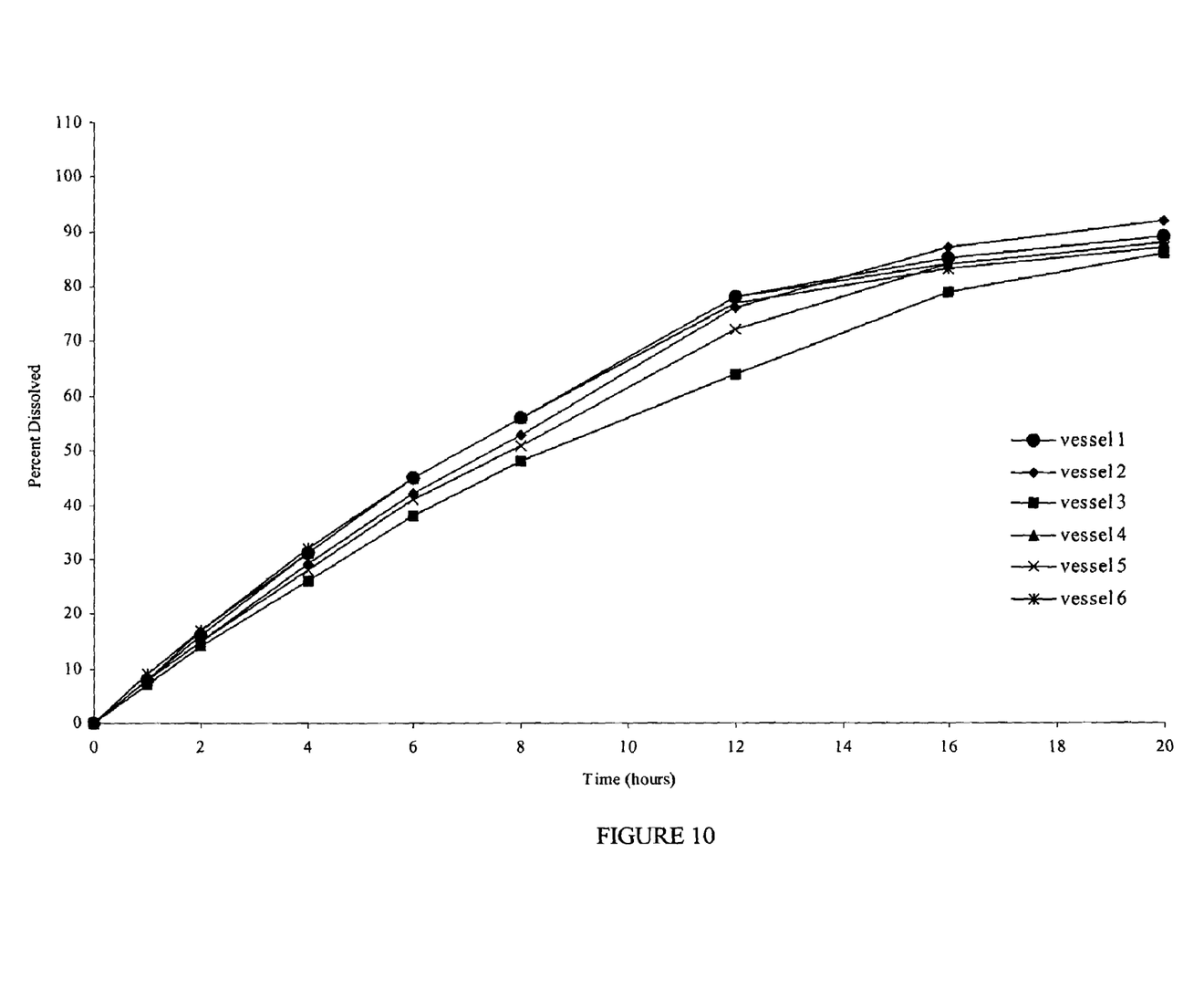

FIGS. 8, 9 and 10 show the dissolution profiles for the various coating levels. As the coating level increases, the release rate decreases showing a change in the shape of the release curve from pseudo first order to zero order. As the coating level increases, the release rate decreases, demonstrating that a customized release profile can be achieved by varying the coating thickness.

What is claimed is:

1. An oral osmotic pharmaceutical delivery dosage form comprising: (a) a semipermeable wall; and (b) a single, solid core composition within said wall consisting essentially of: at least one pharmaceutically active agent that has solubility limitations due to inherent hydrophobicity or to high drug load, wherein high drug load means that at least 30% by weight of the dosage form is the at least one active agent, and, homogenously mixed with said pharmaceutically active agent, (1) a non-swelling osmotic agent, and (2) from 1 to 10% by weight of the core of meglumine, as a solubilizer, wherein said wall maintains its integrity during pharmaceutical delivery and has at least one passageway through it, connecting the core of the dosage form with the external environment, wherein the size of the passageway(s) is from 100μ to 1000μ.

2. An oral osmotic pharmaceutical delivery dosage form comprising: (a) a solid core comprising a pharmaceutically active agent that has solubility limitations due to inherent hydrophobicity or to high drug load, wherein high drug load means that at least 30% by weight of the dosage form is the at least one active agent, a non-swelling osmotic agent and from 1 to 10% by weight of the core of meglumine, as a solubilizer, wherein the pharmaceutically active agent, non-swelling osmotic agent and meglumine are all present as a homogeneous mixture in at least one layer, and when said core comprises more than one layer, each layer comprises at least one pharmaceutically active agent, and (b) a semipermeable wall that surrounds the core, maintains its integrity during pharmaceutical delivery and has at least one passageway through it, connecting the core of the dosage form with the external environment, wherein a size of the passageway(s) is from 100μ to 1000μ.

3. The osmotic dosage form of claim 1 or claim 2, wherein the semipermeable wall is comprised of a water insoluble polymer of cellulose acylate, cellulose ethyl ether, cellulose diacylate, cellulose triacylate, cellulose acetate, cellulose diacetate, cellulose triacetate, mono-, di- and tricellulose alkyls, or mono-, di- and tricellulose aroyls.

4. The osmotic dosage form of claim 3, wherein the water insoluble polymer is cellulose acetate.

5. The osmotic dosage form of claim 1 or claim 2, wherein the semipermeable wall also contains 0.01% to 20% by weight of a plasticizer.

6. The osmotic dosage form of claim 5, wherein the plasticizer is dibenzyl phthalate, dihexyl phthalate, butyl octyl phthalate, straight chain phthalates of six to eleven carbons, di-isononyl phthalate, di-isodecyl phthalate, triacetin, dioctyl azelate, epoxidized tallate, tri-isoctyl trimellitate, tri-isononyl trimellitate, sucrose acetate isobutyrate, or epoxidized soybean oil.

7. The osmotic dosage form of claim 4, which further comprises a plasticizer selected from triethyl citrate (TEC), propylene glycol (PG), a mixture of TEC and PG in ratios ranging from 25% TEC/75% PG to 75% TEC/25% PG, Tween 80 or other polyoxyethylene sorbitan esters, triacetin, diethyl phthalate, polyethylene glycol, mineral oil, tributyl sebacate, and glycerol.

8. The osmotic dosage form of claim 7, wherein the plasticizer is TEC.

9. The osmotic dosage form of claim 1 or claim 2, wherein the semi-permeable wall represents a weight gain to the dosage form of from about 2% to about 15%.

10. The osmotic dosage form of claim 1 or claim 2, wherein the core further comprises a high HLB surfactant as a co-solubilizer.

11. The osmotic dosage form of claim 1 to claim 2, wherein the pharmaceutically active agent is one or more of albendazole, albuterol, acyclovir, adriamycin, carbamazepine, oxcarbazepine, amiodarone, amlodipine, amphetamine, amphotericin B, atorvastatin, atovaquone, azithromycin, baclofen, bicalutamide, busulfan, butenafine, calcipotriene, calcitriol, camptothecin, capsaicin, carotenes, celecoxib, cerivastatin, chlorpheniramine, cimetidine, ciprofloxacin, cisapride, cetirizine, clarithromycin, clemastine, codeine, cyclosporin, danazol, dantrolene, dexchlorpheniramine, digoxin, dirithromycin, donepezil, efavirenz, ergotamine, etodolac, etoposide, famotidine, fentanyl, finasteride, fluconazole, flurbiprofen, fluvastatin, fosphenyloin, frovatriptan, gabapentin, gemfibrozil, glibenclamide, glyburide, glimepiride, griseofulvin, halofantrine, ibuprofen, irinotecan, isotretinoin, itraconazole, ivermectin, ketoconazole, ketorolac, lamotrigine, angiotensin converting enzyme (ACE) or NEP inhibitors, fenofibrate, fexofenadine, flutamide, glipizide, glyburide, isradipine, loratadine, lovastatin, melphalan, nifedipine, leflunomide, loperamide, lycopenes, mifepristone, mefloquine, methadone, methoxsalen, metronidazole, miconazole, midazolam, miglitol, mitoxantrone, nabumetone, nalbuphine, naratriptan, nelfinavir, nilutamide, nizatidine, oxaprozin, paclitaxel, pentazocine, pioglitazone, pizotefin, pravastatin, probucol, pyridostigmine, raloxifene, rofecoxib, repaglinide, rifapentine, rimexolone, rizatriptan, rosiglitazone, saquinavir, sibutramine, sildenafil citrate, simvastatin, sirolimus, spironolactone, sumatriptan, tacrine, tacrolimus, tamoxifen, tamsulosin, targretin, tazarotene, teniposide, terbinafine, tiagabine, tizanidine, topiramate, topotecan, toremifene, tramadol, tretinoin, troglitazone, trovafloxacin, verteporfin, vigabatrin, vitamin A, vitamin D, vitamin E, vitamin K, zafirlukast, zileuton, zolmitriptan, zolpidem, zopiclone, proton pump inhibitors such as lansoprazole, esomeprazole, omeprazole, and rabeprazole, MAP kinase inhibitors, ICE inhibitors such as pralnacasan, pseudoephedrine, indomethacin, naproxen, estrogens, testosterones, steroids, phenyloin, ergotamines and cannabinoids, pharmaceutically acceptable salts, isomers, prodrugs and derivatives thereof.

12. The osmotic dosage form of claim 11, wherein the pharmaceutically active agent is one or more of albuterol, acyclovir, adriamycin, carbamazepine, oxcarbazepine, cyclosporin, griseofulvin, angiotensin converting enzyme (ACE) or NEP inhibitors, fenofibrate, fexofenadine flutamide, glipizide, glyburide, isradipine, loratadine, lovastatin, melphalan, nifedipine, proton pump inhibitors, MAP kinase inhibitors, pralnacasan, pseudoephedrine, indomethacin, naproxen, estrogens, testosterones, steroids, phenyloin, sumatriptan, ergotamines or cannabinoids, or pharmaceutically acceptable salts, isomers, or prodrugs or derivatives thereof.

13. The osmotic dosage form of claim 12, wherein the pharmaceutically active agent is one or more of carbamazepine, oxcarbazepine, fenofibrate, fexofenadine, glipizide, lorsoprasole, esomeprazole and rabeprozole, or pharmaceutically acceptable salts, isomers, or prodrugs or derivatives thereof.

14. The osmotic dosage form of claim 1 or claim 2, wherein the pharmaceutically active agent is one or more of diltiazem HCl, verapamil HCl, metoprolol, succinate, quetiapine fumarate, valganciclovir HCl, theophylline, and naproxene sodium.

15. The osmotic dosage form of claim 14, wherein the pharmaceutically active agent is glipizide.

16. The composition of claim 1 or claim 2, wherein the osmotic agent is selected from a group consisting of xylitiol, mannitol, sorbitol, inositol, sucrose, lactose, dextrose, maltodextrin and salts.

17. The dosage form of claims 1 and 2, comprising from 4% to 6% by weight of the core of meglumine.

* * * * *